United States Patent [19]

Secrist, III

[11] Patent Number: 4,794,174
[45] Date of Patent: Dec. 27, 1988

[54] 5'-DEOXY-5'-SUBSTITUTED ADENOSINES

[75] Inventor: John A. Secrist, III, Birmingham, Ala.

[73] Assignee: Southern Research Institute, Birmingham, Ala.

[21] Appl. No.: 13,061

[22] Filed: Feb. 10, 1987

[51] Int. Cl.$^4$ ........................ C07H 19/16; C12P 19/28
[52] U.S. Cl. ........................................ 536/26; 536/23; 536/24; 536/27; 514/43; 514/45; 514/46
[58] Field of Search ........................................... 536/26

[56] References Cited

U.S. PATENT DOCUMENTS 3,954,726  5/1976  Fiecchi ................................... 536/26
4,242,505 12/1980  Kawahara ............................... 536/26
4,621,056 11/1986  Gennari ................................. 536/26

OTHER PUBLICATIONS

Khomutou et al. (II), Bioorg. Khim., vol. 12 (12), pp. 1662–1674 (1986).
Kolb et al., *Liebigs Ann. Chem.*, (1985), pp. 1036–1040.

Primary Examiner—J. R. Brown
Assistant Examiner—L. Eric Crane
Attorney, Agent, or Firm—Roylance, Abrams, Berdo & Goodman

[57] ABSTRACT

In accordance with this invention, there are provided 5'-deoxy-5'-substituted adenosines having the formula

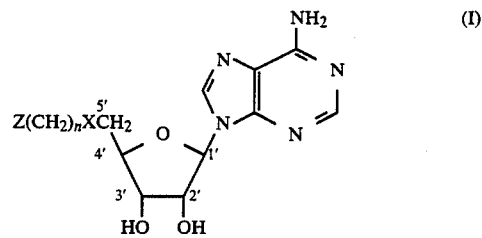

wherein X is a member selected from the group consisting of NH, NCH$_3$, S, or

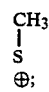

n is an integer from 2–4; and Z is a member selected from the group consisting of:

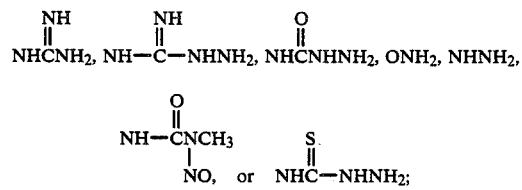

provided that when X is NH, S or CH$_3$—S $\oplus$, then Z is not ONH$_2$. These compounds show activity as inhibitors of AdoMet-DC.

11 Claims, No Drawings

5'-DEOXY-5'-SUBSTITUTED ADENOSINES

BACKGROUND OF THE INVENTION

This invention relates to certain 5'-deoxy-5'-substituted adenosines which are useful as inhibitors of S-adenosylmethionine decarboxylase (AdoMet-DC).

In recent years, there has been considerable research carried out that relates to the polyamine biosynthetic pathway. The polyamines putrescine, spermidine and spermine are known to be required for normal cell growth and differentiation, and it has been shown that interference with polyamine metabolism can lead to therapeutic effects, e.g., antiviral, antiparasitic or anticancer effects. See "Recent advances in the biochemistry of polyamines in eukaryotes", Pegg, *Biochem. J.* (1986) Vol. 234, pps. 239-262 and "S-ADENOSYLMETHIONINE DECARBOXYLASE AS TARGET OF CHEMOTHERAPY", Janne et al (1985), *Advances in Enzyme Regulation*, Vol. 24, pps. 125-139, the disclosures of which are incorporated herein by reference.

Kolb et al, *Liebigs Ann. Chem.*, (1985), pps. 1036-1040; Khomutov et al, *Bioorg. Khim.*, (1983), Vol. 9, pps. 130-131; and Artamonova et al, *Bioorg. Khim.*, (1986), Vol. 12, pps. 206-212 all disclose 5'-deoxy-5'-substituted adenosines. Kolb et al discloses such compounds having the structure:

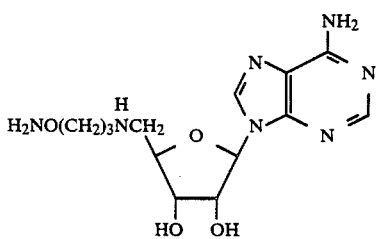

and the two latter articles disclose such compounds having the structure

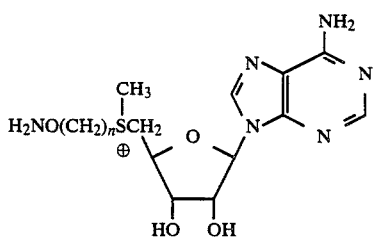

wherein n=2 or 4. The latter two articles note that their compounds are inhibitors of AdoMet-DC.

SUMMARY OF THE INVENTION

In accordance with this invention, there are provided 5'-deoxy-5'-substituted adenosines having the formula

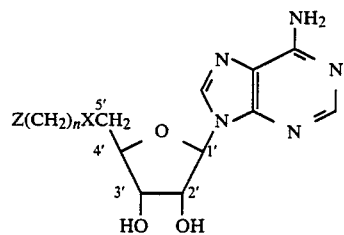

wherein X is a member selected from the group consisting of NH, NCH$_3$, S, or

n is an integer from 2-4; and Z is a member selected from the group consisting of:

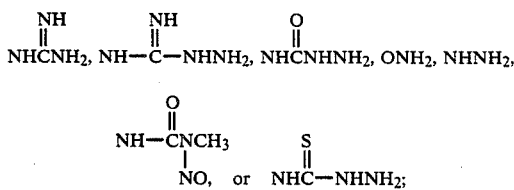

provided that when X is NH, S or CH$_3$—S⊕, then Z is not ONH$_2$.

Specific examples of such compounds, the preparation of which will be discussed hereinafter, are as follows:

TABLE 1

| X | n | Z |
|---|---|---|
| NCH$_3$ | 3 | NH<br>‖<br>NHCNH$_2$ |
| NH | 3 | NH<br>‖<br>NHCNH$_2$ |
| NCH$_3$ | 3 | S<br>‖<br>NHCNHNH$_2$ |
| NCH$_3$ | 3 | O<br>‖<br>NHCNCH$_3$<br>\|<br>NO |
| NCH$_3$ | 3 | O<br>‖<br>NHCNHNH$_2$ |
| NCH$_3$ | 3 | ONH$_2$ |
| NCH$_3$ | 2 | ONH$_2$ |
| NCH$_3$ | 2 | O<br>‖<br>NHCNHNH$_2$ |
| NCH$_3$ | 2 | O<br>‖<br>NHCNCH$_3$<br>\|<br>NO |
| NCH$_3$ | 3 | NH<br>‖<br>NHCNHNH$_2$ |

TABLE 1-continued

| X | n | Z |
|---|---|---|
| NCH$_3$ | 3 | NHNH$_2$ |
| S | 3 | NHC(O)NHNH$_2$ |

The compounds of this invention show activity as inhibitors of AdoMet-DC.

DETAILED DESCRIPTION OF THE INVENTION

To prepare the compounds of this invention, an adenosine derivative with a leaving group at C-5' and with the 2'- and 3'-hydroxyls either blocked or unblocked, depending upon later steps, is treated with the appropriate amine, either the direct side chain precursor, or a simple amine, which after introduction into the nucleoside, is alkylated on nitrogen with a side chain precursor. At this stage, the side chain either ends with an alcohol or primary amine, or is deblocked (i.e., phthalimide to amino) to be one of these two groups. The various end groups are then introduced by standard methodology. If necessary, the 2', 3'-blocking group is then removed to complete the synthesis. The specific procedures for certain compounds are presented in the examples which follow. In these examples, MeOH, EtOH, DMF, THF, Me$_2$CO, and Et$_2$O stand for, respectively, methyl alcohol, ethyl alcohol, N,N-dimethylformamide, tetrahydrofuran, acetone, and ethyl ether. All percentages recited in the examples, unless otherwise identified, refer to yield of product. The underlined numbers in the examples, except for those numbers in the headings which indicate a quantity of complexed solvent (e.g., H$_2$O and H$_2$SO$_4$), refer to the compounds indicated by the corresponding numbers in Table 2 which follows. In Table 2, Ad stands for the group

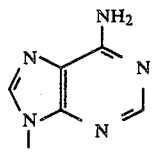

TABLE 2

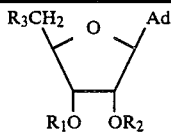

(1) $R_1 = R_2 = H$; $R_3 = Cl$ (2) $R_1, R_2 = {>}C(CH_3)_2$; $R_3 = OTs$ (3) $R_1, R_2 = H$;
$R_3 = N(CH_3)CH_2CH_2CH_2NHC(=NH)NH_2 \cdot 1.5H_2SO_4$ (4) $R_1, R_2 = {>}C(CH_3)_2$; $R_3 = N(CH_3)CH_2CH_2CH_2OH$ (5) $R_1, R_2 = {>}C(CH_3)_2$;
$R_3 = N(CH_3)CH_2CH_2CH_2O$-phthalimide (6) $R_1 = R_2 = H$; $R_3 = N(CH_3)CH_2CH_2CH_2ONH_2 \cdot 1.5H_2SO_4$ (7) $R_1, R_2 = {>}C(CH_3)_2$; $R_3 = N(CH_3)CH_2CH_2OH$ (8) $R_1, R_2 = {>}C(CH_3)_2$;
$R_3 = N(CH_3)CH_2CH_2O$-phthalimide (9) $R_1 = R_2 = H$; $R_3 = N(CH_3)CH_2CH_2ONH_2 \cdot 1.5H_2SO_4$

(10) $R_1, R_2 = {>}C(CH_3)_2$; $R_3 = NHCH_2CH_2CH_2NH_2$

(11) $R_1 = R_2 = H$; $R_3 = NHCH_2CH_2CH_2NHC(=NH)NH_2 \cdot 1.5H_2SO_4$

(12) $R_1 = R_2 = H$; $R_3 = N(CH_3)CH_2CH_2CH_2NH_2$

(13) $R_1 = R_2 = H$; $R_3 = N(CH_3)CH_2CH_2NH_2$

(14) $R_1 = R_2 = H$; $R_3 = N(CH_3)CH_2CH_2NHC(O)N(NO)CH_3$

(15) $R_1 = R_2 = H$; $R_3 = N(CH_3)CH_2CH_2CH_2NHC(O)N(NO)CH_3$

(16) $R_1 = R_2 = H$; $R_3 = N(CH_3)CH_2CH_2NHC(O)NHNH_2$

(17) $R_1 = R_2 = H$;
$R_3 = N(CH_3)CH_2CH_2CH_2NHC(O)NHNH_2 \cdot 1.75H_2SO_4$

(18) $R_1, R_2 = {>}C(CH_3)_2$; $R_3 = NHCH_3$

(19) $R_1, R_2 = {>}C(CH_3)_2$;
$R_3 = N(CH_3)CH_2CH_2CH_2$-phthalimide

TABLE 2-continued

(20) $R_1, R_2 = {>}C(CH_3)_2$; $R_3 = N(CH_3)CH_2CH_2CH_2NH_2$

(21) $R_1, R_2 = {>}C(CH_3)_2$; $R_3 = N(CH_3)CH_2CH_2CH_2N{=}C{=}S$

(22) $R_1, R_2 = {>}C(CH_3)_2$;

$$R_3 = N(CH_3)CH_2CH_2CH_2NH\overset{\overset{S}{\|}}{C}NHNH_2$$

(23) $R_1 = R_2 = H$; $R_3 = N(CH_3)CH_2CH_2CH_2NH\overset{\overset{S}{\|}}{C}NHNH_2$

(24) $R_1, R_2 = {>}C(CH_3)$;

$R_3 = N(CH_3)CH_2CH_2CH_2N(CO_2tBu)NHCO_2tBu$

(25) $R_1 = R_2 = H$;
$R_3 = N(CH_3)CH_2CH_2CH_2NHNH_2 \cdot 1.5H_2SO_4$

(26) $R_1, R_2 = {>}C(CH_3)_2$;

$$R_3 = N(CH_3)CH_2CH_2CH_2NH\overset{\overset{S}{\|}}{C}NH\overset{\overset{O}{\|}}{C}C_6H_5$$

(27) $R_1, R_2 = {>}C(CH_3)_2$; $R_3 = N(CH_3)CH_2CH_2CH_2NH\overset{\overset{S}{\|}}{C}NH_2$

(28) $R_1, R_2 = {>}C(CH_3)_2$;

$$R_3 = N(CH_3)CH_2CH_2CH_2NH\overset{\overset{SCH_3}{|}}{C}{=}NH \cdot HI$$

(29) $R_1 = R_2 = H$;

$$R_3 = N(CH_3)CH_2CH_2CH_2NH\overset{\overset{NH}{\|}}{C}{-}NHNH_2 \cdot 1.5H_2SO_4$$

(30) $R_1 = R_2 = H$; $R_3 = SCH_2CH_2CH_2NH_2$

(31) $R_1 = R_2 = H$;

$$R_3 = SCH_2CH_2CH_2NH\overset{\overset{O}{\|}}{C}NHNH_2 \cdot H_2SO_4$$

EXAMPLE 1

5'-Deoxy-5'-[N-methyl-N-(3-guanidinopropyl)-]aminoadenosine, sesquisulfate (3.1.5H₂SO₄)

A solution of 2',3'-O-methylethylidene-5'-O-p-toluenesulfonyladenosine (2) (2.40 g, 5.18 mmol) in 15 mL N-methyl-1,5-propanediamine was stirred at room temperature for 60 hours. The diamine was removed in vacuo and the residue was purified by flash chromatography, eluting with 77:20:3 CHCl₃/MeOH/NH₄OH. Removal of the solvent and lyophilization left an off-white solid (1.38 g, 3.66 mmol, 71%), positive nihydrin test. Although two isomers were presumed present, they could not be separated at this stage by TLC or HPLC. Thus, 500 mg (1.33 mmol) of the mixture was dissolved in 1N NaOH (5 mL) and S-ethyl thiourea hydrobromide (490 mg, 2.66 mmol) was added. The pH was adjusted to 10.5 with 1N NaOH and the solution stirred at room temperature eight days. The pH was then lowered to ~7 with 6N HCl and the water was evaporated in vacuo. The residue was separated by flash chromatography (6:3:1 CHCl₃/MeOH/NH₄OH) to give 145 mg and 175 mg, respectively, of the two isomers, $R_f$ 0.39 and 0.35 (6:3:1 CHCl₃/MeOH/N-H₄OH). Both showed m/e 420 (M+1)⁺ in their mass spectra (FAB). The slower-moving isomer (173 mg) was stirred 24 hours in 1N H₂SO₄ to remove the isopropylidene group. The sulfate salt was precipitated by adding 14 mL of EtOH, and again precipitated from H₂O with EtOH. The fine powder was dissolved in 3 mL H₂O and lyophilized to give 105 mg (0.212 mmol, 16% overall) of 3.

¹H NMR coupling experiments confirmed the structure (e.g., the NH proton coupled with the single adjacent methylene group *only*). ¹H NMR (Me₂SO-d₆) δ 1.70–1.82 (m, 2, —NHCH₂CH₂), 2.61 (s, 3, N—CH₃), 2.90 (t, 2, —N(CH₃)CH₂), 3.13 (6, 2, —NHCH₂), 3.20–3.45 (m, 2, C₅·H₂), 4.20 (t, 1, C₃·H), 4.27 (t, 1, C₄·H), 4.72 (t, 1, C₂·H), 5.95 (d, 1, C₁·H), 6.90–7.55 (m, 5, —C(NH)NH₂H₂SO₄), 7.34 (s, 2, N⁶H), 7.64 (br s, 1, NH), 8.18 (s, 1, C₂H), 8.36 (s, 1, C₈H); MS (FAB): m/z 379 (M+1)⁺. Anal. Calcd for C₁₅H₂₅N₉O₃·0.25 EtOH·1.3H₂O·1.5H₂SO₄: C, 33.16; H, 5.76; N, 22.45. Found: C, 33.03; H, 5.75; N, 22.24.

EXAMPLE 2

5'-Deoxy-2'3'-O-methylethylidene-5'-[N-methyl-N-(3-hydroxypropyl)]aminoadenosine (4)

2',3'-O-Methylethylidene-5'-O-tosyladenosine (2, 3.00 g, 6.5 mmol) was stirred for 40 hours in 3-(N-methylamino)propanol (3.0 g, 33.7 mmol) and DMF (15 mL). Most of the solvent was evaporated (50° C., 1 torr), and the residue was dissolved in CHCl₃ (50 mL). The solution was washed with saturated aqueous NaHCO₃ (50 mL); the aqueous solution had to be back-extracted with CHCl₃ several times to recover all the nucleoside. The combined organic layers were dried (Na₂SO₄), and then concentrated to about 20 mL. Application to a silica gel column and elution with 4:1 CHCl₃/MeOH gave 1.77 g (4.67 mmol; 72%) of 4 as a foam. FABMS: m/z 379 (M+1)⁺. ¹H-NMR (Me₂SO-d₆) δ 8.34 (s, 1, H-2), 8.18 (s, 1, H-8), 7.34 (s, 2, 6-NH₂), 6.14 (d, 1, H-1'), 5.50 (dd, 1, H-2'), 4.96 (dd, 1, H-3'), 4.40 (br s, 1, OH), 4.24 (dt, 1, H-4'), 3.38 (t, 2, —CH₂OH), 2.6–2.3 (m, 2, H₂-5'), 2.38 (m, 2, N(CH₃)CH₂—), 2.14 (s, 3, N—CH₃), 1.53 and 1.33 (2 s, 6, C(CH₃)₂), 1.50 (q, 2, —CH₂CH₂OH). This material was suitable for use as an intermediate.

EXAMPLE 3

2',3'-O-Methylethylidene-5'-deoxy-5'-[N-methyl-N-[3-(O-phthalimido)propyl]]aminoadenosine (5)

Triphenylphosphine (70 mg, 0.265 mmol), N-hydroxyphthalimide (45 mg, 0.265 mmol) and 2',3'-O-methylethylidene-5'-deoxy-5'-[N-methyl-N-(3-hydroxypropyl)]-aminoadenosine 4 (100 mg, 0.264 mmol) were dissolved in 4 mL dry THF under a nitrogen atmosphere. Diethyl azodicarboxylate (45 μL, 0.29 mmol) was then added. After stirring 2 hours at room temperature, the solvent was removed on a rotary evaporator. The residue was purified by flash chromatography (1:3

CH$_2$Cl$_2$/Me$_2$CO) to give 85 mg (0.162 mmol; 61%) of 5 as a white foam. A portion was precipitated from CHCl$_3$ with petroleum ether for an analytical sample. FAB MS: m/z 524 (M+1)$^+$; 389 (M-adenine)$^+$; 290 (M—Phtho(CH$_2$)$_3$NCH$_3$—)$^+$. $^1$H-NMR (CDCl$_3$) δ 1.39 and 1.60 (2 s, 6, C(CH$_3$)$_2$), 1.88 (q, 2, —OCH$_2$C$\overline{H_2}$—), 2.28 (s, 3, —N(C$\overline{H_3}$)—), 2.50-2.75 (2 m, 4, C$_5$, and H$_2$ and —N(C$\overline{H_3}$—CH$_2$—), 4.22 (m, 2, PhthOCH$_2$—), 4.40 (dt, 1, H-4'), 4.98 (dd, 1, H-3'), 5.50 (dd, 1, H-2'), 5.64 (s, 2, 6—NH$_2$), 6.07 (d, 1, H-1'), 7.80 (m, 4, Phth), 7.98 and 8.36 (2 s, 2, C$_8$H and C$_2$H). Anal. Calcd for C$_{15}$H$_{29}$N$_7$O$_4$: C, 57.35; H, 5.58; N, 18.73. Found; C, 57.07; H, 5.68; N, 18.62.

EXAMPLE 4

5'-Deoxy-5'-[N-methyl-N-[3-aminooxy)propyl]-]aminoadenosine sesquisulfate 0.67H$_2$O (6.1.5H$_2$SO$_4$)

A solution of 5 (245 mg, 0.468 mmol) in 8 mLN H$_2$SO$_4$ was heated 1.5 hours at 60° C. After cooling, the volume was reduced to one-half on a rotary evaporator. Addition of 15 mL EtOH precipitated a fine solid which was collected by centrifugation. The solid was dissolved in 3 mL H$_2$O and again precipitated with 10 mL EtOH. Finally, the product was allowed to slowly precipitate from 10 mL of 50% aq. EtOH; the resulting film was lyophilized from 3 mL H$_2$O to give 158 mg (0.308 mmol; 66%) as a light solid, m.p. dec. from 155° C. FABMS: m/z 354 (M+1)$^+$. $^1$H-NMR (Me$_2$SO-d$_6$) δ 8.38 (s, 1, H-8), 8.20 (s, 1, H-2), 7.40 (s, 2, 6—NH$_2$), 5.98 (d, 1, H-1'), 4.74 (t, 1, H-2'), 4.34 (m, 1, H-4'), 4.22 (t, 1, H-3'), 3.73 (m, 2, —CH$_2$ONH$_2$), 3.68-3.44 (m, 2, H$_2$-5'), 3.16 (t, 2, —N(CH$_3$)C$\overline{H_2}$—), 2.79 (s, 3, N—CH$_3$), 1.93 (m, 2, —CH$_2$CH$_2$ON$\overline{H_2}$). $^{13}$C-NMR (Me$_2$SO-d$_6$) δ 155.89 (C-6), 152.32 (C-2), 148.89 (C-4), 140.33 (C-8), 119.38 (C-5), 88.64 (C-1'), 78.15 (C-4'), 72.22 and 71.80 (C-3' and C-2'), 71.43 (—CHONH$_2$), 56.89 (N(CH$_3$)CH$_2$), 53.13 (C-5'), 22.27 (—N(CH$_3$)CH$_2$CH$_2$). N—CH$_3$ possibly seen as shoulder of Me$_2$SO-d$_6$ peak at 39.94. Anal. Calcd for C$_{14}$H$_{23}$N$_7$O$_4$.1.5H$_2$SO$_4$.0.7H$_2$O: C, 32.77; H, 5.38; N, 19.11. Found: C, 33.12; H, 5.44; N, 18.75.

EXAMPLE 5

5'-Deoxy-2'3'-O-Methylethylidene-5'-[N-methyl-N-(2-hydroxyethyl)]aminoadenosine (7)

This synthesis was accomplished in similar manner to 4, starting with 3.00 g of the tosylate (2) and 3.0 g of commercially available 2-(N-methylamino)ethanol. The product was obtained as an oil, 1.66 g (4.85 mmol; 70%). FABMS: m/z 365 (M+1)$^+$. $^1$H-NMR (Me$_2$SO-d$_6$) δ 8.34 (s, 1, H-2), 8.18 (s, 1, H-8), 7.34 (s, 2, 6—NH$_2$), 6.14 (d, 1, H-1'), 5.49 (dd, 1, H-2'), 4.97 (dd, 1, H-3'), 4.25 (dt, 1, H-4'), 3.44 (t, 2, —CH$_2$OH), 2.7-2.4 (m, 2, H$_2$-5'), 2.43 (m, 2, —CH$_2$CH$_2$O$\overline{H}$), 2.22 (s, 3, N—CH$_3$), 1.55 and 1.34 (2 s, 6, C(CH$_3$)$_2$).

EXAMPLE 6

5'-Deoxy-2'3'-O-methylethylidene-5'-[N-methyl-N-[2-(O-phthalimido)ethyl]aminoadenosine (8)

To a solution of 7 (540 mg, 1.48 mmol), N-hydroxyphthalimide (270 mg, 1.60 mmol), and triphenylphosphine (420 mg, 1.60 mmol) in 25 mL THF was added diethyl azodicarboxylate (0.275 mL, 1.75 mmol). After stirring 1 hour, the solution was diluted with 50 mL CHCl$_3$ and washed with 40 mL 2% aqueous Na$_2$CO$_3$ (to remove excess N-hydroxyphthalimide), then with brine. After drying the organic layer (Na$_2$SO$_4$), the solvents were evaporated in vacuo and the residue purified by plug filtration over 20 g silica gel (9:1 CHCl$_3$/MeOH) to give 680 mg (1.33 mmol; 90%) of a white foam, homogeneous by TLC. FABMS: m/z 510 (M+1)$^+$. $^1$H-NMR (CDCl$_3$) δ 8.35 (s, 1, H-2), 807 (s, 1, H-8), 7.78 (m, 4, phth), 6.11 (d, 1, H-1'), 5.87 (s, 2, 6-NH$_2$), 5.50 (dd, 1, H-2'), 5.05 (dd, 1, H-3'), 4.43 (dt, 1, H-4'), 4.30 (t, 2, —CH$_2$OPhth), 2.90 (t, 2, —N(CH$_3$)CH$_2$—), 2.90-2.70 (m, $\overline{2}$, H-5'), 2.40 (s, 3, N—CH$_3$), 1.62 and 1.41 (2 s, 6, C(CH$_3$)$_2$). Anal. Calcd for C$_{24}$H$_{27}$N$_7$O$_6$: C, 56.58; H, 5.34; N, 19.24. Found: C, 56.24; H, 5.34; N, 18.91.

EXAMPLE 7

5'-Deoxy-5'-[N-methyl-N-[2-(aminooxy)ethyl]-]aminoadenosine, sesquisulfate dihydrate (9.1.5H$_2$SO$_4$)

Removal of the protecting groups from 8 and purification were carried out in essentially the same manner as with 6, starting with 200 mg of 8 (0.393 mmol) in 7 mL NH$_2$SO$_4$ to yield 140 mg (0.268 mmol; 68%) of 9, m.p. dec. from 150° C. FABMS m/z 340 (M+1)$^+$.$^1$H-NMR (Me$_2$SO-d$_6$) δ 8.42 (s, 1, H-2), 8.24 (s, 1, H-2), 7.64 (s, 2, 6-NH$_2$), 5.98 (d, 1, H-1'), 4.67 (t, 1, H-2'), 4.36 (m, 1, H-4'), 4.23 (t, 1, H-3'), 4.04 (m, 2, —CH$_2$ONH$_2$), 3.62 (m, 2, H$_2$-5'), 3.43 (m, 2, —N(CH$_3$)C$\overline{H_2}$), 2.84 (s, 3, N-CH$_3$). $^{13}$C-NMR (Me$_2$SO-d$_6$) δ 155.$\overline{14}$ (C-6), 151.48 (C-2), 148.69 (C-4), 140.50 (C-8), 119.21 (C-5), 88.64 (C-1'), 78.13 (C-4'), 72.41 and 71.82 (C-3' and C-2'), 68.16 (—CH$_2$ONH$_2$), 57.42 (—N(CH$_3$)CH$_2$), 53.49 (C-5'), 40.53 (N-CH$_3$). Anal. Calcd for C$_{13}$H$_{21}$N$_7$O$_4$.1.5H$_2$SO$_4$.2H$_2$O: C, 29.88; H, 5.40; N, 18.76; S. 9.20. Found: C, 29.94; H, 5.43; N, 18.71; S, 9.13. UV (H$_2$O) pH 1, λ$_{max}$ 257 nm (14,400); pH 7, 259 (14,600); pH 13, 259 (14,800).

EXAMPLE 8

5'-Deoxy-5'-[N-3-(guanidino)propyl]aminoadenosine sesquisulfate (11.1.5H$_2$SO$_4$)

To a solution of 2',3'-O-methylethylidene-5'-deoxy-5'-[N-3-aminopropyl]aminoadenosine monohydrate (10.H$_2$O) (500 mg, 1.38 mmol) in 4 mL of 1N NaOH was added S-ethylthiourea hydrobromide (510 mg, 2.76 mmol). The pH was raised to 10.5 with NNaOH, and maintained 5 days at room temperature. The pH was adjusted to 7 with NHCl, the water removed in vacuo, and the residue purified by flash chromtography (6:3:1 CHCl$_3$/MeOH/NH$_4$OH). This gave a white glass (130 mg) which was dissolved in 4 mL 1N H$_2$SO$_4$ and stirred 25 hours. The product was precipitated by adding 15 mL EtOH. The solid was collected, washed, and dried to yield 55 mg (0.11 mmol; 8% overall yield). FAB MS: m/z 366 (M+1)$^+$. $^1$H-NMR (Me$_2$SO-d$_6$) δ 1.78 (m, 2, —NHCH$_2$CH$_2$—), 2.98 (t, 2, —C$_5$·H$_2$NHCH$_2$—), 3.17 (m, 2, —C($=$NH)NHCH$_2$—), 3.25-3.50 (2 m, 2, 5'—CH$_2$), 4.22 (m, 1, H-4'), 4.27 (t, 1, H-3'), 4.73 (m, 1, H-2'), 5.97 (d, 1, H-1'), 7.38 (br s, 2, 6—NH$_2$), 7.57 (t, 1, —C($=$NH)NHCH$_2$—), 8.18 and 8.37 (2 s, 2, C$_2$H and C$_8$H). Anal. Calcd for C$_{14}$H$_{23}$N$_9$O$_3$0.2EtO$\overline{H}$.1.5-H$_2\overline{O}$.1.8H$_2$SO$_4$: C, 29.92; H, 5.37; N, 21.81. Found: C, 29.88; H, 5.47; N, 21.70.

EXAMPLE 9

5'-Deoxy-5'-[N-methyl-N-(2-aminoethyl)]aminoadenosine monohydrate (12)

A solution of 5'-deoxy-5'-chloroadenosine (1, 5.10 g, 17.9 mmol) in 5.0 g of N-methylethylenediamine and 5 mL DMF was heated for 24 hours at 80° C. The solvents were evaporated (30° C., 1 mm Hg), and the residue separated by flash chromatography (300 g silica gel, 6:3:1 CHCl$_3$/MeOH/NH$_4$OH). The faster-traveling isomer was further purified by ion exchange (Dowex 50WX4 NH$_4$), eluting the product with 3M NH$_4$OH. The pure fractions were combined and evaporated to dryness on a rotary evaporator. The oil residue was dissolved in 10 mL H$_2$O and lyophilized to give an off-white solid, 1.51 g, (4.42 mmol; 25%). This compound was judged suitable for further use by MS, $^1$H-NMR, and TLC. FABMS: m/z 324 (M+1)$^+$. $^1$H-NMR (Me$_2$SO-d$_6$) δ 8.34 (s, 1, H-2), 8.16 (s, 1, H-8), 7.28 (s, 2, 6-NH$_2$), 5.87 (d, 1, H-1'), 4.64 (t, 1, H-2'), 4.13 (t, 1, H-3'), 4.00 (m, 1, H-4'), 2.8–2.55 (m, 2, H$_2$-5'), 2.60 (t, 3, —CH$_2$NH$_2$), 2.40 (m, 2, —CH$_2$CH$_2$NH$_2$), 2.21 (s, 3, N—$\overline{\text{C}}$H$_3$).

EXAMPLE 10

5'-Deoxy-5'-[N-methyl-N-[2-[[(methylnitrosoamino)-carbonyl]amino]ethyl]]aminoadenosine (14)

To a cold solution of 12.H$_2$O (250 mg, 0.73 mmol) in 3 mL of DMF was added, 2,4,5-trichlorophenyl N-methyl-N-nitrosocarbamate (210 mg, 0.75 mmol) in one portion. The solution was allowed to warm to room temperature and stirred 3 hours. Evaporation of the DMF in vacuo and flash chromatography (1:1 EtOAc/MeOH) gave 230 mg of a white foam, homogeneous by TLC. FABMS: m/z 410 (M+1)$^+$. The unstable compound was immediately employed for the next step.

EXAMPLE 11

5'-Deoxy-5'-[N-methyl-N-[3-[[(methylnitrosoamino)-carbonyl]amino]propyl]aminoadenosine (15)

A solution of 5'-deoxy-5'-[N-methyl-N-(3-aminopropyl)]aminoadenosine dihydrate (13.H$_2$O prepared and purified as with 12) (470 mg, 1.26 mmol) in 2 mL DMF was added to a cold solution of 2,4,5-trichlorophenyl N-methyl-N-nitrosocarbamate (410 mg, 0.1.45 mmol) in 5 mL DMF. After 2 hours, the DMF was evaporated (room temperature, 1 mm). The residue was purified by flash chromatography (1:1 CHCl$_3$/MeOH), giving 410 mg (0.97 mmol; 77%) of 15, homogeneous by TLC, positive Griess test for N-nitrosoureas. A portion of the sample was recrystallized from 2-propanol-ether for an analytical sample. FAB MS: m/z 424 (M+1)$^+$; 364 (M-N(NO)CH$_3$). $^1$H-NMR (Me$_2$SO-d$_6$) δ 1.69 (q, 2, —NHCH$_2$CH$_2$), 2.18 (s, 3, —N—CH$_3$), 2.42 (m, 2, —N(CH$_3$)CH$_2$—), 2.63 (2 m, 2, 5'—CH$_2$), 3.06 (s, 3, —N(NO)$\overline{\text{C}}$H$_3$), 3.30 (t, 2, —NH$\overline{\text{C}}$H$_2$), 3.99 (dd, 1, C$_{4'}$H), 4.10 ($\overline{\text{dd}}$, 1, C$_{3'}$H), 4.66 (dd, 1, $\overline{\text{C}_{2'}}$H), 5.19 (d, 1, C$_{3'}$HOH), 5.44 (d, 1, $\overline{\text{C}_{2'}}$HOH), 6.05 (d, 1, $\overline{\text{C}_{1'}}$H), 7.26 (s, 2, N$^6$H$_2$), 8.14 (s, 1, C$_8$H), 8.32 (s, 1, C$_2$H), 8.78 (t, 1, —NH$\overline{\text{C}}$H$_2$). Anal. Calcd for C$_{16}$H$_{25}$N$_9$O$_5$.0.2(CH$_3$)$_2$CHOH.0.2Et$_2$O.0.8H$_2$O: C, 44.97; H, 6.55; N, 27.13. Found: C, 44.66; H, 6.55; N, 27.08.

EXAMPLE 12

5'-Deoxy-5'-[N-methyl-N-[2-(hydrazinecarboxamido)ethyl]aminoadenosine, sesquisulfate dihydrate (16.1.5H$_2$SO$_4$)

A solution of 14 (220 mg, 0.538 mmol) and hydrazine monohydrate (120 μL, 5 equiv) in 3 mL ethanol was stirred 18 hours at room temperature. The solvent was evaporated and the residue dried under vacuum (<1 mm) for 5 hours. The compound was then dissolved in 2 mL of NH$_2$SO$_4$ and precipitated by the addition of 10 mL of EtOH. The precipitation process was repeated three times using 2:1 EtOH/H$_2$O to leave the pure product as an oil. Lyophilization from 3 mL H$_2$O gave a light solid, 130 mg (0.230 mmol; 43%), m.p. dec. from 148° C. FABMS: m/z 382 (M+1)$^+$. $^1$H-NMR (Me$_2$DO-d$_6$) δ 8.37 (s, 1, H-2), 8.19 (s, 1, H-8), 7.38 (s, 2, 6-NH$_2$), 6.98 (t, 1, —NHC(=O)NHNH$_2$), 5.98 (d, 1, H-1'), 4.70 (t, 1, H-2'), 4.34 (m, 1, H-4'), 4.21 (t, 1, H-3'), 3.75–3.45 (m, 2, H$_2$-5'), 3.39 (m, 2, —CH$_2$NHC—), 3.18 (t, 2, —N(CH$_3$)CH$_2$), 2.84 (s, 3, N—$\overline{\text{C}}$H$_3$). $^{13}$C-NMR (D$_2$O, dioxane as ext. reference, T=80° C.) δ 160.21 (C=O), 151.82 (C-4), 149.05 (C-6), 146.81 (C-2), 144.10 (C-8), 120.18 (C-5), 90.80 (C-1'), 79.14 (C-4'), 73.78 and 72.61 (C-2' and C-3'), 58.88 (—N(CH$_3$)CH$_2$), 57.35 (C-5'), 41.91 (N—CH$_3$), 35.84 (—N(CH$_3$)CH$_2$CH$_2$—); UV (H$_2$O) λ$_{max}$ pH 1, 256 nm (14,800); pH 7, 260 (14,600); pH 13, 260 nm (15,100). Anal. Calcd for C$_{14}$H$_{23}$N$_9$O$_4$.1.5H$_2$SO$_4$.2H$_2$O: C, 29.79; H, 5.36; N, 22.33; S, 8.52. Found: C, 29.91; H, 5.35; N, 22.43; S, 8.57.

EXAMPLE 13

5'-Deoxy-5'-[N-methyl-N-[3-(hydrazinecarboxamido)-propyl]]aminoadenosine, 1.75 sulfate dihydrate (17.1.75 H$_2$SO$_4$)

A solution of 15 (195 mg, 0.45 mmol) and hydrazine monohydrate (225 μL, 4.6 mmol) was stirred for 15 hours in methanol (5 mL) at room temperature. The solvent was removed in vacuo and excess hydrazine was evaporated under high vacuum. The residue was stirred 5 minutes in 3 mL 1N H$_2$SO$_4$, then precipitated by adding 15 mL EtOH. The solid was washed with cold EtOH, dissolved in 3 mL H$_2$O, and again precipitated by adding 10 mL EtOH (stored in refrigerator overnight. The resulting sticky film was lyophilized from 3 mL H$_2$O to give 235 mg of 17 as a fluffy white solid (0.39 mmol, 87%). FAB MS: m/z 396 (M+1)$^+$. $^1$H-NMR (Me$_2$SO-d$_6$) δ 1.80 (m, 2, —NHCH$_2$CH$_2$—), 2.79 (s, 3, —N(CH$_3$), 3.02–3.18 (2 m, 4, —NH$\overline{\text{C}}$H$_2$, —NHCH$_2$CH$_2$—), 3.48 and 3.68 (2 m, 2, 5'—CH$_2$), 4.25 (t, 1, H-3'), 4.36(m, 1, H-4'), 4.77 (t, 1, H-2'), 6.00 (d, 1, H-1'), 6.96 (br s, —NHCH$_2$—), 7.42 (br s, 2, N$^6$H$_2$), 8.21 and 8.40 (2 s, 2, C$_2$H and C$_8$H). $^{13}$C-NMR (Me$_2$SO-d$_6$) δ 24.20 (—NHCH$_2$HC$_2$), 36.23 (—NHCH$_2$—), 40.00 (—NCH$_3$), 53.64 (—N(CH$_3$)CH$_2$—), 56.80 (C$_{5'}$), 71.80 and 72.24 (C$_{2'}$ and C$_{3'}$), 78.27 (C$_{4'}$), 88.54 (C$_{1'}$), 119.25 (C$_5$), 140.29 (C$_8$), 148.86 (C$_4$), 152.40 (C$_2$), 155.88 (C$_6$), 158.58 (N—C=O). Anal. Calcd for C$_{15}$H$_{25}$N$_9$O$_4$.1.75H$_2$SO$_4$.2H$_2$O: C, 29.88; H, 5.43; N, 20.90; S, 9.30. Found: C, 29.66; H, 5.46; N, 20.88; S, 9.31. UV (H$_2$O) pH 1, λ$_{max}$ 14,500 (257 nm); pH 7, 14,400 (259); pH 13, 15,000 (259).

EXAMPLE 14

5'-Deoxy-2',3'-O-methylethylidene-5'-[N-methyl-N-(3-aminopropyl)]aminoadenosine (20)

A solution containing 5'-deoxy-2',3'-O-methylethylidene-5'-methylaminoadenosine (18, 380 mg, 1.19 mmol), N-(3-bromopropyl)phthalimide (320 mg, 1.20 mmol), and diisopropylethylamine (0.21 mL, 1.20 mmol) in 1 mL of DMF was stirred at room temperature for 17 hours. The solution was diluted with chloroform (20 mL) and washed with 1N Na$_2$CO$_3$. The aqueous layer was extracted with chloroform (20 mL), and the combined organic layers were dried (Na$_2$SO$_4$) and the solvent removed under reduced pressure. The residue was purified by flash chromatography (9:1 chloroform-methanol) to afford 320 mg (53%) of the desired 19; $^1$H-NMR (CDCl$_3$) δ 1.40 and 1.60 (2 s, 6, C(CH$_3$)$_2$), 1.80 (m, 2, C—CH$_2$C), 2.26 (s, 3, NCH$_3$), 2.44 (t, 2, N(CH$_3$)CH$_2$), 2.53, 2.64 (2 m (8 lines), 2, 5'—CH$_2$), 3.71 (m, 2, Phth—CH$_2$), 4.38 (m, 1, H-4'), 5.02 (dd, 1, J$_{3',4'}$=6.5 Hz), H-3'), 5.51 (dd, 1, J$_{2',3'}$=6.5 Hz, H-2'), 6.00 (br s, 2, NH$_2$), 6.08 (d, 1, J$_{1',2'}$=2.0 Hz, H-1'), 7.70, 7.84 (2 m, 4, phthalimide), 8.00, 8.35 (2 s, 2, H-2,8). This material was used directly in the next step.

To a boiling solution of 19 (140 mg, 0.277 mmol) in EtOH (5 mL) was added hydrazine hydrate (70 μL, 1.435 mmol), and the solution heated for 1 hour. After the reaction was cooled to room temperature, phthalhydrazide was filtered off, washing with EtOH. The filtrate was evaporated to dryness, and the product was purified by preparative thin layer chromatography (80:20:3 CH$_2$Cl$_2$/CH$_3$OH/conc. NH$_4$OH) to afford 83 mg (80%) of the desired 20; MS (FAB) 378 (M+1)$^+$. An analytical sample was obtained as the tripicrate: $^1$H-NMR (Me$_2$SO-d$_6$) δ 1.34, 1.59 (2 s, 6, C(CH$_3$)$_2$), 1.88 (m, 2, C—CH$_2$—C), 2.80 and 3.14 (2 br m, 7, —CH$_2$N(CH$_3$)CH$_2$—), 3.60 (br m, 2, CH$_2$NH$_2$), 4.61 (m, 1, H-4'), 5.05 (dd, 1, J$_{3',4'}$=4.0 Hz, H-3'), 5.33 (dd, 1, J$_{2',3'}$=6.0 Hz, H-2'), 6.36 (d, 1, J$_{1',2'}$=2.0 Hz, H-1'), 7.72 (br s, NH$_3^\oplus$), 8.44, 8.63 (2 s, 2, H-2,8), 8.59 (s, 6, picrate ArH). Anal. Calcd for C$_{17}$H$_{27}$N$_7$O$_3$·3C$_6$H$_3$N$_3$O$_7$: C, 39.48; H, 3.41; N, 21.05. Found: C, 39.26; H, 3.43; N, 20.95.

Larger runs of both steps (gram quantities) were purified by flash chromatography. The amine was used directly, not as the picrate salt.

EXAMPLE 15

2',3'-O-Methylethylidene-5'-deoxy-5'-[N-methyl-N-[3-(isothiocyanato)propyl]]aminoadenosine (21)

A solution of 2',3'-O-methylethylidine-5'-deoxy-5'-[N-methyl-N-(3-aminopropyl)]aminoadenosine monohydrate (20) (400 mg, 1.06 mmol) in 10 mL H$_2$O was added to 10 mL CHCl$_3$ and stirred vigorously. Thiophosgene (100 μl, 1.32 mmol) in 5 mL CHCl$_3$ was added dropwise over 30 minutes. The pH was then raised to 9 by addition of 2N NaOH. The organic layer was separated and dried (MgSO$_4$), and the solvent was evaporated (reduced pressure). The residue was filtered through a plug of 10 g silica gel (1:3 CH$_2$Cl$_2$/Me$_2$CO) to remove a polar impurity. Removal of the solvents in vacuo and drying left 275 mg (0.65 mmol; 62%) of 21; homogeneous by TLC and suitable for the next step. FAB MS: m/z 420 (M+1)$^+$, 285 (M-adenine)$^+$. IR (CHCl$_3$ film): 2112 cm$^{-1}$, s (N=C=S stretch).

EXAMPLE 16

2',3'-O-Methylethylidene-5'-deoxy-5'-[N-methyl-N-[3-(hydrazinethiocarboxamido)propyl]]aminoadenosine (22)

To a stirred solution of 21 (195 mg, 0.46 mmol) in 5 mL THF was added hydrazine monohydrate (27 μL, 0.56 mmol). After 10 minutes TLC analysis indicated that the reaction was complete. The solvent was evaporated in vacuo and the residue dried, leaving a pale yellow foam, homogeneous by TLC, 210 mg (0.46 mmol, 100%); (6:3:1 CHCl$_3$/MeOH/NH$_4$OH). FAB MS: m/z 452 (M+1)$^+$. $^1$H-NMR (Me$_2$SO-d$_6$) δ 1.34, 1.54 (2 s, 6, C(CH$_3$)$_2$), 1.52–1.82 (m, 2, —NHCH$_2$CH$_2$), 2.16 (s, 3, N—CH$_3$), 2.20–2.44 (m, 3, C$_5$·H and —N(CH$_3$)CH$_2$), 2.54–2.68 (m, 1, H-5'), 3.44 and 3.61 (m and t, 2, —NHCH$_2$), 4.27 (dt, 1, H-4'), 4.42 (br s, 2, —NHNH$_2$), 4.98 (dd, 1, H-3'), 5.49 (dd, 1, H-2'), 6.15 (d, 1, H-1'), 7.34 (s, 2, 6—NH$_2$), 7.91 (br s, 1, —CH$_2$NH), 8.19, 8.35 (2 s, 2, C$_8$H and C$_2$H), 8.55 (s, 1, —NHNH$_2$).

EXAMPLE 17

5'-Deoxy-5'-[N-methyl-[3-(hydrazinethiocarboxamido)-propyl]]aminoadenosine sesquisulfate dihydrate (23.1.5H$_2$SO$_4$)

A solution of 22 (105 mg, 0.233 mmol) in 1N H$_2$SO$_4$ (3 mL) was stirred 20 hours at room temperature. Addition of 15 mL EtOH caused a white precipitate, which was collected and washed. The precipitate was then slowly deposited from ethanol/water, leaving a fine glass. This was lyophilized from 3 mL H$_2$O and dried at 78° C. to give 80 mg (0.133 mmol, 57%) of 3 as a fluffy off-white solid. FAB MS: m/z 412 (M+1)$^+$. $^1$H-NMR (Me$_2$SO-d$_6$) δ 1.80–2.06 (m, 2, —NHCH$_2$CH$_2$—), 2.78 (s, 3, —N—CH$_3$), 3.00–3.30 (m, 2, N(CH$_3$)CH$_2$), 3.30–3.65 (m, 4, H-5' and —NHCH$_2$—), 4.22–4.40 (m, 1, H-4'), 4.28–4.44 (m, 1, H-3'), 4.62–4.88 (m, 1, H-2'), 5.2–6.0 (m, 4, OH, H$_2$O), 6.00 (d, 1, H-1'), 7.36 (s, 2, 6—NH$_2$), 8.03 (br s, 2, —NHNH$_2$), 8.20 and 8.38 (2 s, 2, C$_8$H and C$_2$H). $^{13}$C-NMR (Me$_2$SO-d$_6$) δ 23.60 (—NHCH$_2$CH$_2$), 71.77 (C$_{3'}$), 72.36 (C$_{2'}$), 78.04 (C$_{4'}$), 88.63 (C$_{1'}$), 119.21 (C$_5$), 140.77 (C$_8$), 148.68 (C$_4$), 150.96 (C$_2$), 154.70 (C$_6$), 181.24 (—C=S). UV (H$_2$O): pH 1, λ$_{max}$ 19,600 (247 nm); pH 7, 14,900 (240 nm) and 15,200 (258); pH 13, 15,100 (240) and 16,700 (258). Anal. Calcd for C$_{15}$H$_{25}$N$_9$O$_3$S.1.5H$_2$O: C, 30.09; H, 5.41; N, 21.05; S, 13.38. Found: C, 30.07; H, 5.49; N, 21.01; S, 13.34.

EXAMPLE 18

5'-Deoxy-2',3'-O-methylethylidene-5'-[N-methyl-N-[3-[1,2-bis[(1,1-dimethylethoxy)carbonyl]hydrazino]-propyl]]aminoadenosine (24)

Di-tert-butyl azodicarboxylate (760 mg, 3.30 mmol) was added to 10 mL of THF containing triphenylphosphine (865 mg, 3.30 mmol) and 4 (500 mg, 1.32 mmol). After 4 hours the solvent was evaporated. The residue was purified by chromatography on silica gel in two different systems: first, in 9:1 CHCl$_3$/MeOH, then in 2:1 CH$_2$Cl$_2$/Me$_2$CO. The product thus obtained (as a white foam) was homogeneous by tlc in the above systems. Attempts to recrystallize from various solvents were unsuccessful. Yield: 844 mg (0.99 mmol; 75%). FABMS: m/z 853 (M+1)$^+$. $^1$H NMR (CDCl$_3$) δ 8.07 (s, 1, H-2), 7.94 (s, 1, H-8), 7.9–7.4 (m, 15, Ph), 6.04 (d, 1, H-1'), 5.45 (m, 1, H-2'), 4.99 (m, 1, H-3'), 4.32 (m, 1, H-4'), 3.44 (m, 2, H-5'), 2.56 (m, 2, N(CH$_3$)CH$_2$), 2.36 (m, 2, CH$_2$NNH), 2.22 (s, 3, N(CH$_3$)), 1.66 (m, 2, N(CH$_3$)CH$_2$CH$_2$), 1.60 and 1.38 (2 s, 6, C(CH$_3$)$_2$), 1.43 and 1.45 (2 s, 18, C(CH$_3$)$_3$).

EXAMPLE 19

5'-Deoxy-5'-[N-methyl-N-(3-hydrazinopropyl)-]aminoadenosine sesquisulfate 1.8H$_2$O.0.1EtOH(25.1.5H$_2$SO$_4$)

A mixture of 24 (650 mg, 0.762 mmol) in 20 mL of 1:1 dioxane/1M H$_2$SO$_4$ was heated at 70° C. for 2 hours. The solution was allowed to cool and then extracted with CH$_2$Cl$_2$ (2×20 mL). The aqueous layer was concentrated to about 15 mL on a rotary evaporator at 35° C.; addition of 50 mL of EtOH caused a precipitate. This was then allowed to slowly precipitate from 8 mL at 1:1 EtOH/H$_2$O as a thick oil. Lyophilization from 5 mL H$_2$O and drying gave a fluffy solid, 265 mg (0.492 mmol; 65%), m.p. 145° C. (dec). FABMS: m/z 353

(M+1)+. $^1$H NMR (Me$_2$SO-d$_6$) δ 8.36 (s, 1, H-2), 8.20 (s, 1, H-8), 7.34 (s, 2, 6-NH$_2$), 5.95 (d, 1, H-1'), 4.71 (t, 1, H-2'), 4.28 (m, 1, H-4'), 4.20 (t, 1, H-3'), 3.35 (m, 2, H-5'), 3.01 (t, 2, CH$_2$NHNH$_2$), 2.90 (t, 2, N(Me)CH$_2$), 2.66 (s, 3, N(CH$_3$)), 1.83 (m, 2, CH$_2$CH$_2$NHNH$_2$). $^{13}$C NMR (Me$_2$SO-d$_6$) δ 155.93 (C-6), 152.45 (C-2), 148.85 (C-4), 140.23 (C-8), 119.26 (C-5), 88.57 (C-1'), 78.35 (C-4'), 72.27 (C-2'), 71.82 (C-3'), 57.12 (N(Me)CH$_2$), 53.31 (C-5'), 46.87 (—CH$_2$NHNH$_2$), 20.19 (—CH$_2$CH$_2$NHNH$_2$); UV (H$_2$O) pH 1, λ$_{max}$ 257 nm (14,400); pH 7, 259 (14,600); pH 13, 260 (14,800). Anal. Calcd for C$_{14}$H$_{24}$N$_8$O$_3$.1.5H$_2$SO$_4$.1.8O.0.1EtOH: C, 31.79; H, 5.86; N, 20.88; S. 8.96. Found: C, 31.60; H, 5.76; N, 21.01; S, 9.08.

EXAMPLE 20

5'-Deoxy-2',3'-O-methylethylidene-5'-[N-methyl-N-[3-(benzoylaminothiocarboxamido)propyl]]aminoadenosine (26)

Benzoyl isothiocyanate (335 mg, 2.05 mmol) in 10 mL of THF was added dropwise over 1 hour to a solution of 5'-deoxy-2',3'-O-methylethylidene-5-[N-methyl-N-(3-aminopropyl)]aminoadenosine (20, 755 mg 2.00 mmol) in 25 mL of THF. The solvent was evaporated and the residue purified by flash chromatography (9:1 CHCl$_3$/MeOH) to give the product as a white foam, 930 mg (1.72 mmol; 86%). Most of the compound was used immediately in the next step. FABMS: m/z 541 (M+1)+. $^1$H-NMR (CDCl$_3$) δ 10.88 (s, 1, —CH$_2$NH), 9.04 (s, 1, —C(=S)NH—), 8.33 (s, 1, H-2), 7.96 (s, 1, H-8), 7.4–7.9 (complex m, 5, Ph), 6.07 (d, 1, H-1'), 5.85 (s, 2, 6-NH$_2$), 5.50 (dd, 1, H-2'), 5.00 (dd, 1, H-3'), 4.42 (dt, 1, H-4'), 3.75 (q, 2, —CH$_2$NH—), 2.62 (m, 2, H$_2$-5'), 2.50 (N(CH$_3$)CH$_2$—), 2.30 (s, 3, N—CH$_3$), 1.81 (m, 2, —CH$_2$CH$_2$NH—), 1.60 and 1.36 (2 s, 6, (C(CH$_3$)$_2$).

EXAMPLE 21

5'-Deoxy-2',3'-O-methylethylidene-5'-[N-methyl-N-[3-(aminothiocarboxamido)propyl]]aminoadenosine (27)

Compound 26 (900 Mg, 1.67 mmol) was heated at 75° C. in 10 mL of NNaOH for one hour. The debenzoylated thiourea was extracted with CHCl$_3$ (4×20 mL). The solvent was evaporated and the crude product recrystallized from H$_2$O to give 665 mg (1.50 mmol; 90%), m.p. dec. from 90° C. FABMS: m/z 437 (M+1)+. $^1$H-NMR (CDCl$_3$) δ 8.52 (br s, 1, —NHC=S), 8.34 (s, 1, H-2), 8.00 (s, 1, H-8), 7.1 (br s, 2, C(=S)NH$_2$), 6.27 (s, 2, 6—NH$_2$), 6.07 (d, 1, H-1'), 5.59 (dd, 1, H-2'), 5.02 (m, 1, H-3'), 4.40 (m, 1, H-4'), 3.47 (m, 2, N(CH$_3$)CH$_2$), 2.88 (m, 2, CH$_2$NH), 2.3–2.8 (m, 2, H$_2$-5'), 2.22 (s, 3, N—CH$_3$), 1.62 and 1.40 (2, s, 6, C-(CH$_3$)$_2$), 1.55 (m, 2, —CH$_2$CH$_2$NH—). Anal. Calcd for C$_{18}$H$_{28}$N$_8$O$_3$.0.4H$_2$O: C, 48.72; H, 6.54; N, 25.25. Found: C, 48.86; H, 6.75; N, 25.18.

EXAMPLE 22

5'-Deoxy-2',3'-O-methylethylidene-5'-[N-methyl-N-[3-(methylthiocarboximidamido)propyl]aminoadenosine hydriodide (28)

A solution of 27 (600 mg, 1.35 mmol) and methyl iodide (100 μL, 1.60 mmol) in 10 mL of EtOH was heated in a 50° C. oil bath for one hour. The solution was cooled and the product precipitated with ether to give 584 mg (1.01 mmol; 75%). FABMS: m/z 451 (M+ of cation). $^1$H-NMR (Me$_2$SO-d$_6$) δ 8.36 (s, 1, H-8), 8.18 (s, 1, H-2), 7.36 (s, 2, 6—NH$_2$), 6.18 (d, 1, H-1'), 5.51 (dd, 1, H-2'), 4.96 (dd, 1, H-3'), 4.30 (m, 1, H-4'), 3.19 (t, 2, CH$_2$NH), 2.60 (m, 2, —N(CH$_3$)CH$_2$—), 2.56 (s, 3, S—CH$_3$), 2.38 (m, 2, H$_2$—5'), 2.18 (s, 3, N—CH$_3$), 1.62 (m, 2, —CH$_2$CH$_2$NH—), 1.55 and 1.33 (2 s, 6, C(CH$_3$)$_2$).

EXAMPLE 23

5'-Deoxy-5'-[N-methyl-N-[3-(hydrazinecarboximidamido)propyl]]aminoadenosine, sesquisulfate dihydrate (29.1.5H$_2$-SO$_4$)

A solution of 28 (200 mg, 0.347 mmol) and hydrazne monohydrate (17 μL, 0.350 mmol) was refluxed in 3 mL of EtOH for 2.5 hours, TLC (6:3:1 CHCl$_3$/MeOH/N-H$_4$OH) indicating a small amount of starting material still present, as well as three different products. After cooling the solution, 0.35 mL of 1N NaOH was added. After diluting with 20 mL of H$_2$O, the mixture was extracted with CHCl$_3$ (3×20 mL); this left mainly the slowest-traveling product in the aqueous layer. The water was evaporated at 45° C. on a rotary evaporator and the residue dried. The solid was triturated with 10 mL of EtOH and filtered, the ethanol evaporated, and the residue stirred 18 hours in 1 mL of 1N H$_2$SO$_4$. The product was precipitated with 5 mL of EtOH; two more precipitations from 2:1 EtOH/H$_2$O followed by lyophilization from 2 mL of H$_2$O gave a solid which appeared homogeneous in the above TLC system; 25 mg (0.035 mmol; 10%). $^1$H-NMR confirmed the structure, but revealed a small amount (1–5%) of a nucleoside impurity. FABMS: m/z 395 (M+1)+. $^1$H-NMR (Me$_2$SO-d$_6$) δ 8.37 (s, 1, H-2), 8.18 (s, 1, H-8), 7.35 (s, 2, 6-NH$_2$), 5.95 (d, 1, H-1'), 4.71 (m, 1, H-2'), 4.25 (m, 2, H-2' and H-3'), 3.24 (m, 2, —N(CH$_3$)CH$_2$), 3.15 (m, 2, H$_2$-5'), 2.84 (m, 2, —CH$_2$NH—), 2.56 (s, 3, N—CH$_3$), 1.76 (m, 2, —N(CH$_3$)CH$_2$CH$_2$).

EXAMPLE 24

5'-S-[3-(Hydrazinecarboxamido)propyl]-5'-thioadenosine sulfate, monohydrate (31.H$_2$SO$_4$.H$_2$O)

The free base of 5'-deoxy-5'-(3-aminopropyl)thioadenosine (30) was obtained by applying 750 mg (1.71 mmol) in 5 mL of H$_2$O to a strongly basic anion exchange resin (Bio-Rad AG1×4, OH$^-$; 20 mL bed volume) and eluting with MeOH (200 ml). After drying, the recovered amine weighed 475 mg (1.40 mmol). To this compound in 5 mL of DMF at 0° C. was added 2,4,5-trichlorophenyl-N-methyl-N-nitrosocarbamate (420 mg, 1.48 mmol). After standing one hour, the DMF was evaporated under reduced pressure. The residue was purified by flash chromatography over silica gel (1:1 CHCl$_3$/MeOH). The pure compound thus obtained was stirred overnight with hydrazine monohydrate (2 mL) in 15 mL of THF. The solvent was removed in vacuo; 5 mL of DMF was added, and the solution was again evaporated in vacuo to dryness. The residue was dissolved in 5 mL of 1N H$_2$SO$_4$ and precipitated with 25 mL of EtOH. This last step was repeated using water rather than acid, leaving a clear oil. This oil was lyophilized from 3 mL of H$_2$O to give 583 mg of 31 (1.13 mmol, 81%) as a light solid, m.p. 132°–136° C. (dec). FABMS: m/z 399 (M+1)+. $^1$H NMR (Me$_2$SO-d$_6$ δ 8.44 (s, 1, NHNH$_2$), 8.38 (s, 1, H-2), 8.18 (s, 1, H-8), 7.41 (s, 2, 6—NH$_2$), 7.03 (t, 1, NHC(=O), 5.89 (d, 1, H-1'), 4.75 (t, 1, H-2'), 4.15 (t, 1, H-3'), 4.01 (m, 1, H-4'), 3.10 (m, 2, CH$_2$NH), 2.86 (m, 2, H-5', J$_{5'a,5'b}$=13.9 Hz), 2.50 (m, 2, SCH$_2$), 1.65 (m, 2, SCH$_2$CH$_2$). $^{13}$C NMR (Me$_2$SO-d$_6$) δ 157.24 (C=O), 155.52 (C-6), 152.01 (C-2), 149.24 (C-4), 139.89 (C-8), 118.98 (C-5), 87.32 (C-1'), 83.77 (C-4'), 72.50 (C-2' and C-3'), 38.34 (CH$_2$NH), 33.88 (C-5'), 29.44 (SCH$_2$), 29.01 (SCH$_2$CH$_2$); UV (H$_2$O) $\lambda_{max}$ pH 1, 257 nm (14,400); pH 7, 259 (14,500); pH 13, 259 (14,700). Anal. Calcd for C$_{14}$H$_{22}$N$_8$O$_4$S.H$_2$SO$_4$.H$_2$O: C, 32.68; H, 5.09; N, 21.78; S, 12.46. Found: C, 32.78; H, 5.08; N, 21.78; S, 12.53.

Table 3 lists examples demonstrating the outstanding enzyme inhibitory properties of certain of the compounds prepared in the preceding examples. Some compounds of this invention are markedly better than the compounds currently being used as the standard inhibitors of the enzyme.

TABLE 3[a]

| Effect of Compounds on AdoMet-DC from MRC5 Cells | |
|---|---|
| Compound | ID$_{50}$ ($\mu$M) |
| 25 | 0.008 |
| 16 | 0.60 |
| 22 | 1.8 |

[a]This data was obtained on a crude enzyme preparation. The assay mixture contained AdoMet at a concentration of 30 $\mu$M. Each inhibitor was tested at a series of concentrations. Methylglyoxal bis(guanylhydrazone), ID$_{50}$ 0.2 $\mu$M, was run as a positive control.

Compounds that inhibit AdoMet-DC would be expected to cause a decrease in spermidine and spermine levels, and an increase in putrescine levels. That such an effect is seen is shown in Table 4 with Compound 25.

TABLE 4

Polyamine Levels in L1210 Cells Treated with 25.

| Time of Treatment (hrs) | Cell Number $\times$ 10$^{-5}$ per mL | Polyamine Content (umol/10$^6$ Cells) | | |
|---|---|---|---|---|
| | | Putrescine | Spermidine | Spermine |
| 0 | 0.6 | 0.38 | 2.68 | 1.14 |
| 24 | 3.4 | 0.49 | 3.84 | 0.82 |
| 24 (+100 $\mu$M 25) | 3.2 | 3.16 | 0.58 | 0.20 |
| 48 | 11.4 | 0.22 | 2.74 | 0.69 |
| 48 (+100 $\mu$M 25) | 8.1 | 4.91 | 0.78 | 0.16 |
| 96 | 43 | 0.34 | 2.59 | 0.73 |
| 96 (+100 $\mu$M 25) | 17 | 5.69 | 0.65 | 0.19 |

Table 5 shows in vitro antiviral activity of Compound 25 against cytomegalovirus.

TABLE 5

The Effects of 25 on HCMV Yields in MRC5 Cell Monolayer Cultures

| 25* | Reduction (%) of CPE by 25 at Time of Virus Harvest | CMV Yield | |
|---|---|---|---|
| | | (log$_{10}$ PFU/ml) | (PFU/ml) |
| 1000 $\mu$M | 0 | 1.4 $\times$ 10$^2$ | 2.2 |
| 320 | 0 | 1.2 $\times$ 10$^5$ | 5.1 |
| 100 | 0 | 4.2 $\times$ 10$^5$ | 5.6 |
| 32 | 0 | 5.8 $\times$ 10$^5$ | 5.8 |
| 10 | 0 | 6.3 $\times$ 10$^5$ | 5.8 |
| 3.2 | 0 | 5.8 $\times$ 10$^5$ | 5.8 |
| 0 (Virus Controls) | — | 5.7 $\times$ 10$^5$ | 5.8 |

*Treatment with 25 began 72 hours prior to virus adsorption. Culture fluids were replaced with fresh drug and medium 24 hours before virus infection, immediately following virus infection, and 3 days p.i.

What is claimed is:

1. A compound having the formula

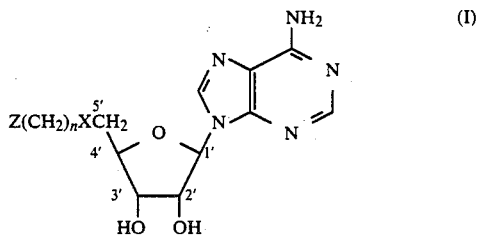

wherein X is a member selected from the group consisting of NH, NCH$_3$, S,

n is an integer from 2-4; and Z is a member selected from the group consisting of:

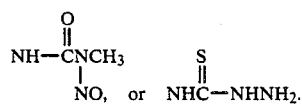

2. A compound as defined in claim 1 wherein X is NCH$_3$, n is 3 and Z is

3. A compound as defined in claim 1 wherein X is NH, n is 3 and Z is

4. A compound as defined in claim 1 wherein X is NCH$_3$, n is 3 and Z is

5. A compound as defined in claim 1 wherein X is NCH$_3$, n is 3 and Z is

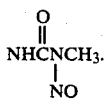

6. A compound as defined in claim 1 wherein X is NCH$_3$, n is 3 and Z is

7. A compound as defined in claim 1 wherein X is NCH$_3$, n is 2 and Z is

8. A compound as defined in claim 1 wherein X is NCH₃, n is 2, and Z is
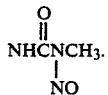
9. A compound as defined in claim 1 wherein X is NCH₃, n is 3 and Z is
10. A compound as defined in claim 1 wherein X is NCH₃, n is 3, and Z is NHNH₂.
11. A compound as defined in claim 1 wherein X is S, n is 3, and Z is
* * * * *